United States Patent
Lysyansky et al.

(10) Patent No.: US 6,994,673 B2
(45) Date of Patent: Feb. 7, 2006

(54) METHOD AND APPARATUS FOR QUANTITATIVE MYOCARDIAL ASSESSMENT

(75) Inventors: Peter Lysyansky, Haifa (IL); Dan Rappaport, Haifa (IL)

(73) Assignee: GE Ultrasound Israel, LTD, Turat-Hacarmel (IL)

(*) Notice: Subject to any disclaimer, the term of this patent is extended or adjusted under 35 U.S.C. 154(b) by 289 days.

(21) Appl. No.: 10/345,580

(22) Filed: Jan. 16, 2003

(65) Prior Publication Data

US 2004/0143189 A1   Jul. 22, 2004

(51) Int. Cl.
*A61B 8/00* (2006.01)

(52) U.S. Cl. .................................... 600/443
(58) Field of Classification Search ............... 600/443, 600/447, 454–456, 407, 409
See application file for complete search history.

(56) References Cited

U.S. PATENT DOCUMENTS

| | | | | |
|---|---|---|---|---|
| 5,195,525 | A * | 3/1993 | Pelc ........................ | 600/410 |
| 5,615,680 | A * | 4/1997 | Sano ....................... | 600/437 |
| 6,517,485 | B2 * | 2/2003 | Torp et al. ............... | 600/438 |
| 6,537,221 | B2 * | 3/2003 | Criton et al. ............ | 600/454 |
| 6,592,522 | B2 * | 7/2003 | Bjaerum et al. ........ | 600/443 |
| 6,721,589 | B1 * | 4/2004 | Zhu et al. ................ | 600/413 |
| 2002/0072674 | A1 | 6/2002 | Criton et al. ............ | 600/454 |
| 2003/0171668 | A1 * | 9/2003 | Tsujino et al. .......... | 600/407 |

FOREIGN PATENT DOCUMENTS

WO   WO 02/045587 A1   6/2002

OTHER PUBLICATIONS

M.J. Ledesma-Carbayo, et al., "Cardiac Ultrasound Motion Detection by Elastic Registration Exploiting Temporal Coherence," Proceedings of the First 2002 IEEE International Symposium on Biomedical Imaging: Marco to Nano (ISBI'02), Washington DC, USA, Jul. 7-10, 2002, vol. II, pp. 585-588.

* cited by examiner

*Primary Examiner*—Francis J. Jaworski
(74) *Attorney, Agent, or Firm*—McAndrews, Held & Malloy, Ltd.; Peter J. Vogel; Michael A. Dellapenna (57) ABSTRACT

Method and apparatus for assessing tissue motion and deformation is provided. Sequential frames of data representative of tissue are accessed. A region of interest is defined on a current frame of data, and first locations of a set of features within the region of interest is identified. Each feature in the set of features identifies a location within the tissue. Second locations of the set of features are located on a consecutive frame of data. Velocity vectors are calculated based on the first and second locations of the set of features, and a continuous spatial and temporal velocity distribution is reconstructed by fitting the velocity vectors. The region of interest is modified on the consecutive frame based on the velocity distribution to follow motion and deformation of the tissue.

21 Claims, 6 Drawing Sheets

METHOD AND APPARATUS FOR QUANTITATIVE MYOCARDIAL ASSESSMENT

BACKGROUND OF THE INVENTION

Certain embodiments of the present invention relate to ultrasound imaging of the human anatomy for the purpose of medical diagnosis. In particular, certain embodiments of the present invention relate to methods and apparatus for assessing tissue motion and deformation, and for improving the assessment of myocardium performance.

The assessment of the myocardium (heart muscles) function using echo-cardiography, or ultrasound, is a crucial indication in the diagnosis of a patient. The outcome of the myocardium evaluation may significantly influence the patient management and course of treatment.

The main part of the myocardium evaluation is based on the observations of experienced echo-cardiographers, who evaluate myocardial dynamics using B-mode ultrasound imaging during a live scan or using a playback of stored cine-loops. The state of each myocardial segment is estimated according to its temporal dynamics. An experienced echo-cardiographer is often able to visually distinguish between working (viable) myocardial segments and segments with different pathologies.

There are disadvantages to relying on visual distinguishing, however. For example, the estimate may be qualitatively flawed as it is based on an impression from moving images. Also, the examination is significantly affected by intra/inter observer variations of diagnostic quality and reproducibility. Thus, the ultrasound may be affected by differing image quality and/or technique. Additionally, significant time is required to achieve the necessary proficiency enabling an echo-cardiographer to reach an accurate diagnosis, and the echo-cardiographer's skills may be negatively impacted if the examination is not performed on a routine basis.

Several quantitative methods exist for heart muscle assessment, such as color kinesis and tissue velocity imaging (TVI). The color kinesis approach is built on B-mode image processing. Automatic edge detection of the left ventricle (LV) allows the estimation of the inward/outward regional translations of the LV wall. This information can be shown in color-coded mapping and can be used for estimating regional myocardial viability. Several drawbacks of color kinesis are that it has limited capabilities to quantify the inner wall performance, and that it does not provide two-dimensional movement and contractility assessment.

TVI is also known as Doppler Velocity Imaging. TVI is based on the Doppler velocity measurements in different locations within a region of interest (ROI). TVI presents a color-coded velocity map of the regional tissue segments. A temporal graph of the mean velocity value of each interrogated point can be shown as well. Further calculations allow the estimation of the local contracting/stretching information which is considered to be a good indicator of the muscle viability. The contractility is presented in color-coded strain and strain rate maps as well as in a graphical form. TVI and its derivatives, strain and strain rate, have been a promising quantitative tool for the viability assessment of the regional myocardium segments, thereby improving the sensitivity and accuracy of inexperienced echo-cardiographers.

TVI, however, also has limitations. The basic TVI imaging shows colorized maps of tissue velocities, but the colorized maps are complicated and therefore difficult to understand. Also, the tissue velocity mapping does not provide the local contractility of the myocardium. The TVI derivatives, strain and strain rate imaging, are regional indicators. Unfortunately the low signal-to-noise ratio experienced with strain and strain rate imaging may not allow stable results.

Furthermore, the Doppler-based methods take temporal information from static Cartesian coordinates. The temporal measurements may mislead the echo-cardiographer because the tissue moves in time, and thus the measurements are made each time in a different location in the tissue.

Finally, the fundamental limitation with Doppler-based methods is that all Doppler methods are one-dimensional. Only the velocity component, which is parallel to the ultrasound scan direction, can be measured. Therefore, it is difficult to assess myocardial regions moving across or almost across ultrasound beams. For example, the assessment of a portion of the apical part of the left ventricle is almost impossible due to a large angle between the ultrasound scan direction and tissue velocity.

Therefore, improving the accuracy of heart muscle assessment by making the assessment more objective and quantitative would have a significant benefit. Also, having a method available for verifying the results of the assessment is desirable.

BRIEF SUMMARY OF THE INVENTION

In accordance with at least one embodiment, a method for assessing tissue motion and deformation is provided. The method includes accessing sequential frames of data representative of tissue. A region of interest is defined on a current frame of data, and first locations of a set of features within the region of interest is identified on the current frame. Each feature in the set of features identifies a location within the tissue. Second locations of the set of features are located on a consecutive frame of data. Velocity vectors are calculated based on the first and second locations of the set of features, and a continuous spatial and temporal velocity distribution is reconstructed by fitting the velocity vectors. The region of interest is modified on the consecutive frame based on the velocity distribution to follow motion and deformation of the tissue.

In accordance with at least one embodiment, a method of assessing left ventricle function is provided. The method includes accessing stored frames of data representative of at least one heart cycle. A region of interest including an outline along an endocardium is identified on a current frame of data. First locations of features representing the endocardium are identified within the region of interest on the current frame. Second locations of the features are estimated on at least one adjacent frame of data, and the region of interest is modified on at least one adjacent frame of data based on the first and second locations to follow motion and deformation in the left ventricle.

In accordance with at least one embodiment, an ultrasonic system for assessing tissue motion and deformation is provided. The system includes a transmitter driving transducers within a probe to emit pulsed ultrasonic signals into a body. A receiver receives echoes which are backscattered from tissue within the body and detected by the transducers. A memory stores the echoes as sequential frames of data. A processor accesses the sequential frames from the memory and defines a region of interest on a current frame. The processor identifies first locations of a set of features on the current frame within the region of interest and locates second locations of the set of features on a consecutive frame. Velocity vectors are calculated based on the first and second locations, and a continuous spatial and temporal velocity distribution is reconstructed by fitting the velocity vectors. The processor modifies the region of interest on the consecutive frame based on the velocity distribution to follow motion and deformation of the tissue.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

Figure 1:
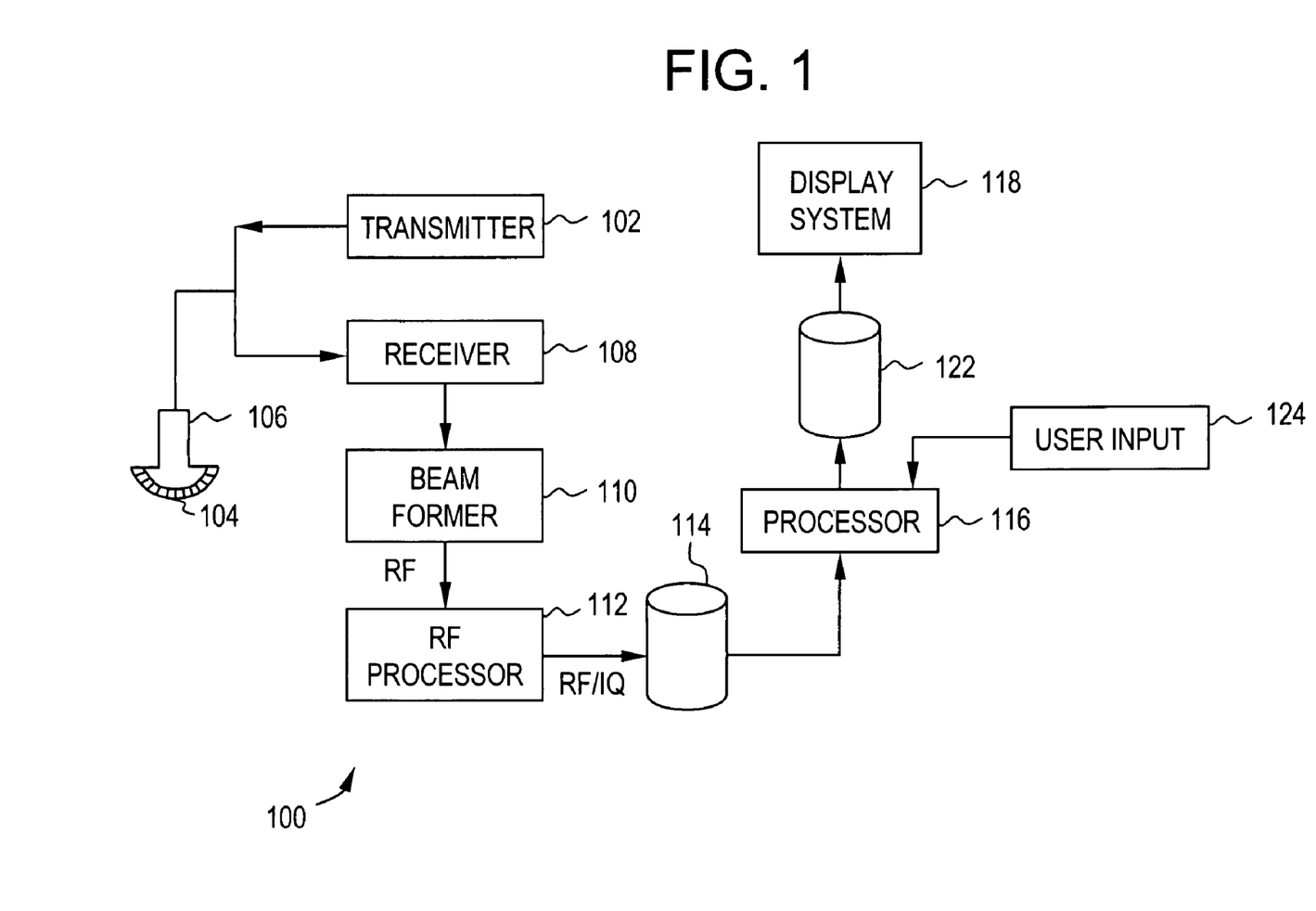
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives transducers 104 within a probe 106 to emit pulsed ultrasonic signals into a body. The ultrasonic signals are backscattered from structures in the body, like blood cells or muscular tissue, to produce echoes which return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage.

The ultrasound system 100 also includes a processor 116 to process the acquired ultrasound information (i.e., RF signal data or IQ data pairs) and prepare frames of ultrasound information for display on display system 118. The processor 116 is adapted to perform one or more processing operations on the acquired ultrasound information according to a plurality of selectable ultrasound modalities. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation. The display system 118 includes at least one monitor. The monitor may be black and white, but preferably the monitor is capable of displaying ultrasound data in color.

The ultrasound system 100 often continuously acquires ultrasound information at a frame rate that exceeds 50 frames per second—the approximate perception rate of the human eye. The acquired ultrasound information is displayed on the display system 118. An image buffer 122 or other storage device is included for storing processed frames of acquired ultrasound information that are not scheduled to be displayed immediately. The frames of ultrasound information are stored in a manner to facilitate their retrieval according to the order or time of acquisition. The image buffer 122 may comprise any known data storage medium.

The system 100 further includes user input 124, which may comprise a keyboard, trackball, and the like. The user input 124 may be used by the echo-cardiographer to enter patient data, select protocols, and select ultrasound data to process and display on display system 118.

Figure 2:
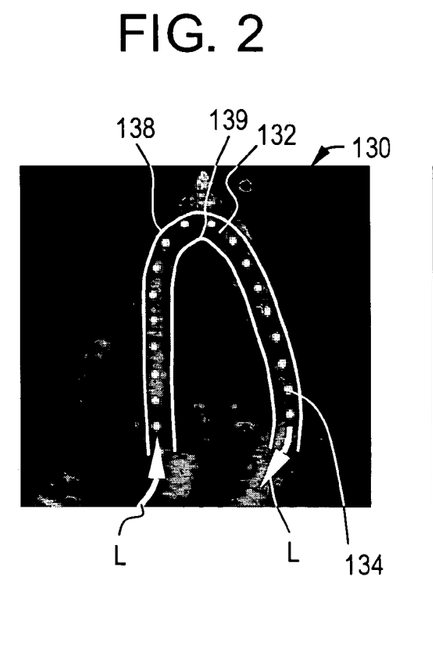
FIG. 2 illustrates a region of interest (ROI) identified on a B-mode frame of ultrasound data representative of myocardium formed in accordance with an embodiment of the present invention.

FIG. 2 illustrates a region of interest (ROI) 132 identified on a B-mode frame 130 of ultrasound data representative of myocardium. Although the following discussion relates to two-dimensional ultrasound images, it should be understood that the same techniques may be applied to three-dimensional ultrasound images. In addition, the techniques may be applied to other applications to assess tissue motion and deformation, and in other imaging modalities, such as tagged MRI images.

The ROI 132 may be entered via user input 124 or can be defined using any automatic myocardial outline procedure such as edge detection. The ROI 132 is selected in accordance with anatomical structure of the heart muscle. The ROI 132 of FIG. 2 is defined by an external border 138 and an internal border 139, which may be displayed on the display system 118. For example, the internal border 139 may define the edge of the endocardium. The external and internal borders 138, 139 may also be illustrated using bullets. Points 134, illustrated as bullets, define a main axis L, or a mid line along the ROI 132, and will be discussed further below. Tissue motions may be described in terms of longitudinal (along) and transverse (across) movements relative to the main axis L. The ultrasound data representing blood is typically displayed as a darker or black pixel, while heart tissue is displayed as a lighter or white pixel. Alternatively, the blood and heart tissue may be displayed using color.

When imaging the myocardium, ultrasound data is typically represented by a temporal sequence of B-mode images or frames 130 including at least one heart cycle. Tissue movements are estimated using frame-by-frame image processing. Unfortunately, a low signal-to-noise ratio characterizes the typical ultrasound image frame 130. The presence of many speckles, also known as speckle noise, erodes the image, and does not allow accurate reconstruction of tissue changes, as the temporal behavior of speckles does not directly reflect the real tissue or blood movements. Therefore, previous attempts to reconstruct temporal deformations of heart tissue using frame-by-frame tracking of ultrasound images has not been successful.

Figure 3:
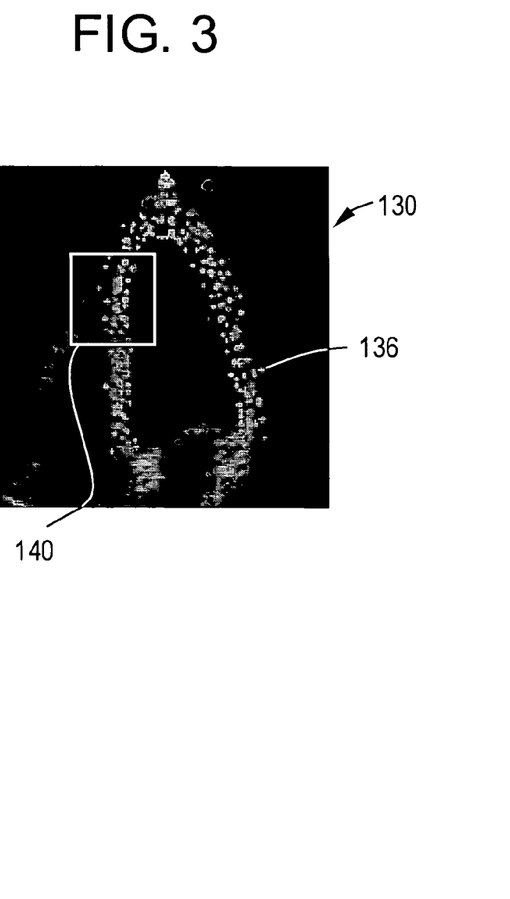
FIG. 3 illustrates the ultrasound image frame of FIG. 2 with the locations of multiple features indicated with small bullets within the ROI (not illustrated) formed in accordance with an embodiment of the present invention.

FIG. 3 illustrates the ultrasound image frame 130 of FIG. 2 with the locations of multiple features 136 indicated with small bullets within the ROI 132 (not illustrated). A portion 140 of the frame 130 is illustrated by a zoom box and will be further discussed below in connection with FIG. 4. The tissue contains many small features 136 which move together with the tissue, forming stable tissue patterns that do not change significantly between adjacent frames 130. The features 136 reflect relatively large non-homogeneities within the tissue, and therefore represent "natural acoustic markers" which are inherent parts of the tissue. The features 136 are temporally stable and represent a real tissue image, as opposed to speckles in the image, which may not be temporally stable over time.

Visual observation by an echo-cardiographer for the purpose of diagnosing myocardial tissue abnormalities may be based on an observation of the features 136. Therefore, an image processing algorithm was developed to recognize and select the features 136 inside the ROI 132. It should be understood that the features 136 maintain their spatial patterns with high probability for at least two or more consecutive frames 130, wherein speckle noise does not. However, the speckle noise and out-of-plane motion caused by patient motion, breathing, or movement of the probe 106, for example, may prevent stability of the features 136 over time. Therefore, the features 136 may be selected in each frame 130 or at some other frequency, such as once per every two or three frames 130.

Figure 4:
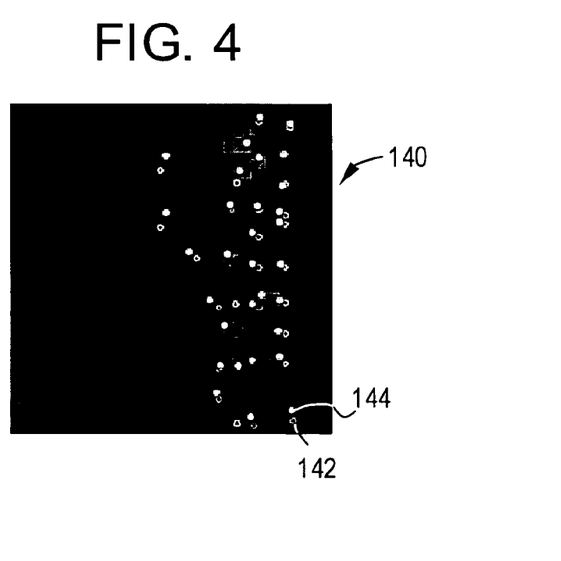
FIG. 4 illustrates a portion of ultrasound image frame of FIG. 3 formed in accordance with an embodiment of the present invention.

FIG. 4 illustrates the portion 140 of the ultrasound image frame 130 of FIG. 3. First locations of a set of features 142 are illustrated with small bullets, and represent features 136 identified (selected) on a current frame 130. Second locations of a set of features 144 are illustrated with large bullets, and represent the same features 136 which are found (tracked) on a next consecutive frame 130. The geometric position of the location of each feature within sets of features 142, 144 changes a small amount between consecutive image frames 130 in accordance with motion of the surrounding tissue. It should be understood that the features 136 and sets of features 142, 144 may be shown for illustration purposes only, and may not be displayed on the display system 118.

Figure 5:
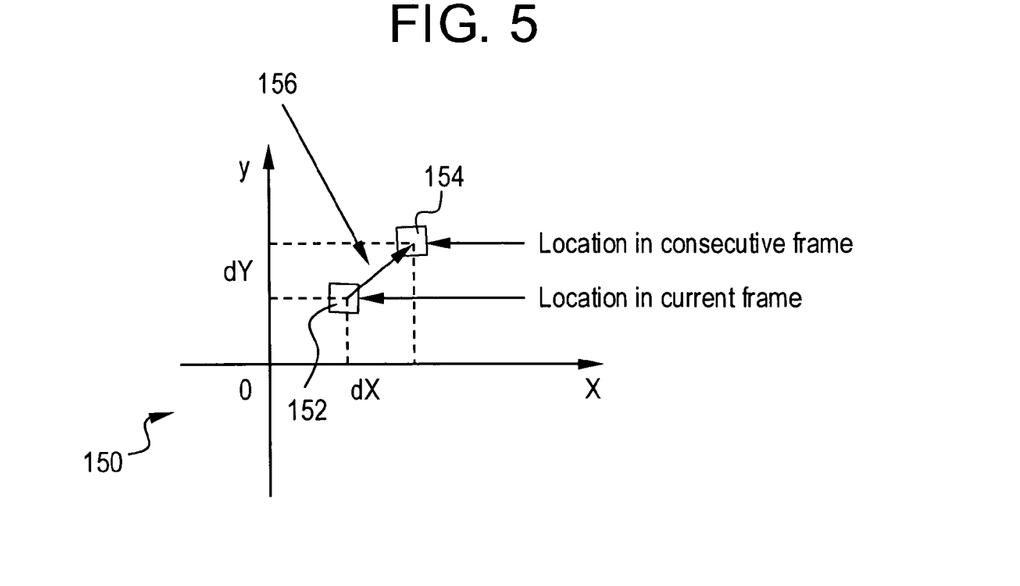
FIG. 5 illustrates a graph of a first location and a second location of the same feature within the myocardium at different times formed in accordance with an embodiment of the present invention.

FIG. 5 illustrates a graph 150 of a first location 152 and a second location 154 of the same feature 136 within the myocardium at different times. The first location 152 of the feature 136 was identified on the current frame 130. The second location 154 of the feature 136 was found on a consecutive frame 130 (previous or next with respect to the current frame 130) by taking the image pattern of features 136 on the current frame 130 and searching for a similar pattern on the consecutive frame 130 using similarity criteria, such as Sum of Absolute Differences (SAD) and/or cross-correlation technique. A quadratic correlation coefficient value grades the similarity of patterns and therefore grades the confidence of the shift estimation for further calculations.

The geometric shift of the feature 136 illustrated by the first and second locations 152, 154 represents local tissue movement. The local tissue velocity can be calculated as a location shift divided by the time between B-mode frames:

$$(Vx, Vy) = (dX, dY) * FR \qquad \text{Equation 1}$$

wherein (Vx,Vy) is 2D velocity vector 156, dX is the distance measured on the X axis from the first location 152 to the second location 154, dY is the distance measured on the Y axis from the first location 152 to the second location 154, and FR is the frame rate used to acquire the current and consecutive frames 130. It should be understood that FIG. 5 illustrates only one feature 136, however, many features 136 exist as illustrated in FIGS. 3 and 4. Therefore, Equation 1 is repeated to calculate the 2D velocity vector 156 for each feature 136 identified on consecutive frames 130, resulting in a discrete set of tissue velocity vectors 156. Relative changes of the mutual distance between neighboring features 136 reflects the tissue's contraction/relaxation (two-dimensional strain rate and strain).

Figure 6:
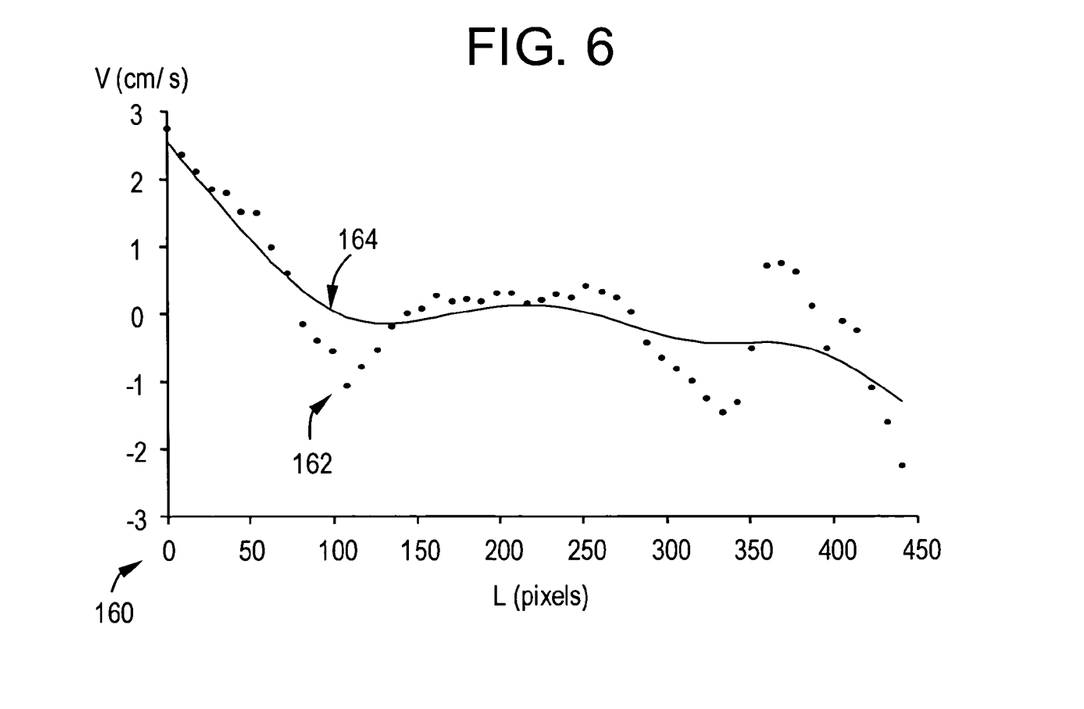
FIG. 6 illustrates the transition from randomly distributed tissue velocities to a continuous velocity distribution formed in accordance with an embodiment of the present invention.

FIG. 6 illustrates the transition from randomly distributed tissue velocities 162 to a continuous velocity distribution. Each bullet on graph 160 represents the velocity 162 of a single feature 136 calculated between two consecutive image frames 130. The position of each feature 136 may be defined relative to the main axis L of the ROI 132 (FIG. 2), such as along (longitudinal to) and across (transverse to) the main axis L. L(pixels) represents the coordinate position of each feature 136 along the main axis L. The transverse coordinate axis is not illustrated, but is used as a second dimension when calculating two-dimensional tissue dynamics.

The tissue dynamics of the myocardium can be described by a relatively smooth spatial function. Therefore, in order to reconstruct full tissue dynamics, the calculated tissue velocities 162 are fit with a continuous function, such as by a smooth function working as a spatial filter, which dramatically increases the signal-to-noise ratio. This approximation allows an accurate presentation of the continuous velocity distribution within the ROI 132 area. Solid curve 164 represents a resulting continuous function of the velocities 162. There are different possibilities for such approximation, such as polynomial fit, spline fit, harmonic fit, and the like. As was mentioned above, correlation values are used as confidential weights in the fitting procedure, thus the resulting velocity representative function is closer to the velocities 162 with higher correlation coefficient (confidence level) and farther from the velocities 162 with lower correlation coefficient.

Figure 7:
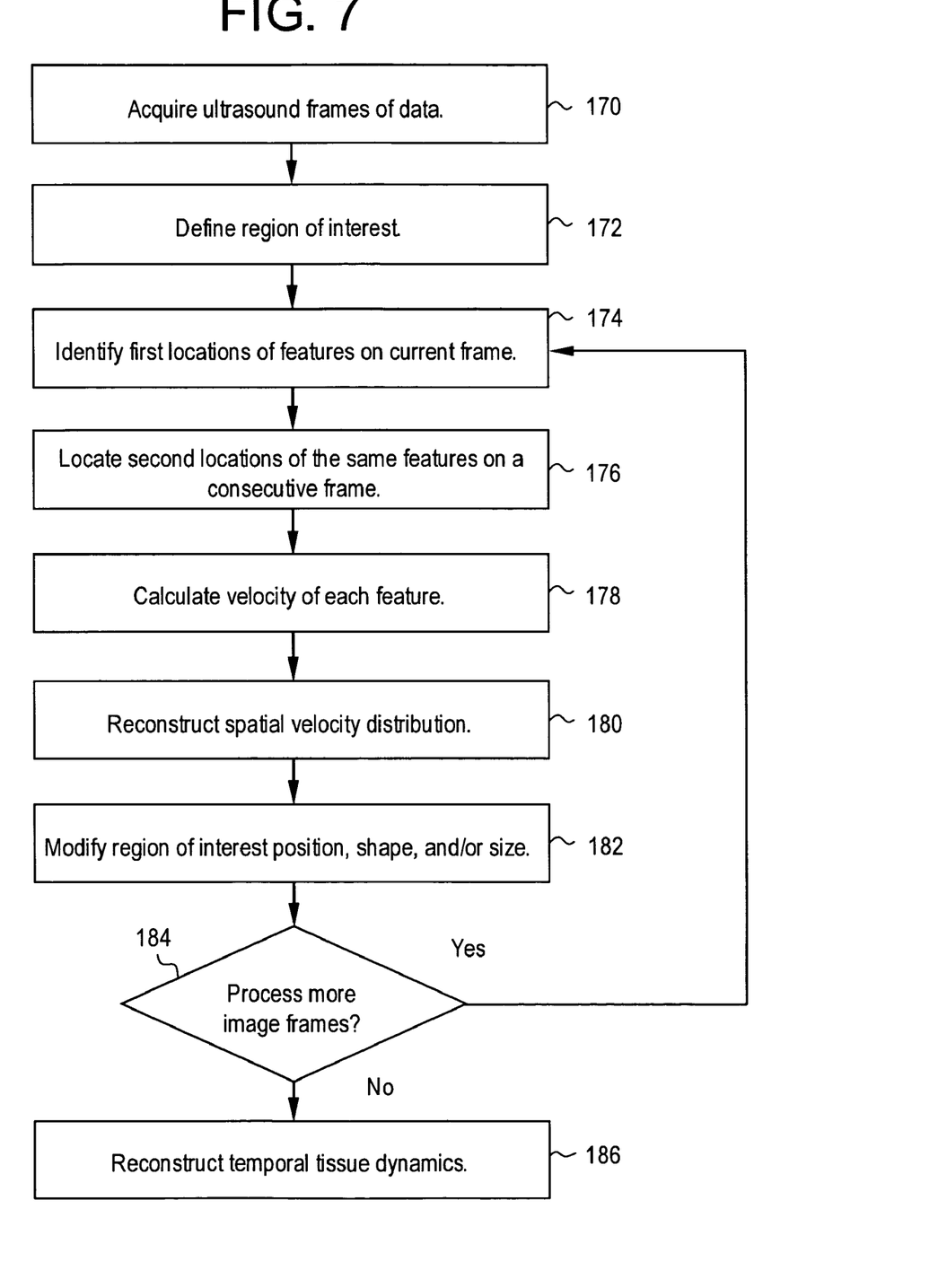
FIG. 7 illustrates a method for quantitative myocardial assessment using features and an ROI in accordance with an embodiment of the present invention.

FIG. 7 illustrates a method for quantitative myocardial assessment using features 136 and ROI 132. In Step 170, ultrasound frames 130 of data are acquired by ultrasound system 100. The frames 130 may include one or more heart cycles, and are stored, by way of example only, in the buffer 114. Alternatively, the frames 130 may be processed in real-time (live scan mode) or near real-time by processor 116 as the frames 130 are acquired.

In Step 172, a region of interest, such as ROI 132, is defined on the current frame 130. An echo-cardiographer may identify the ROI 132 through the user input 124. Alternatively, the ROI 132 may be defined by software algorithms stored in the processor 116.

In Step 174, the processor 116 identifies the first locations of a set of features 142 on the current frame 130, which may be illustrated by bullets as in FIG. 4. In Step 176, the processor 116 locates the second locations of the same features 136 (set of features 144) on a next consecutive frame 130 by using correlation criteria as discussed above. The local tissue velocity is then calculated in step 178 for each feature 136 using Equation 1.

In Step 180, the estimated local tissue velocities are fitted to reconstruct a continuous spatial velocity distribution, such as in FIG. 6.

In Step 182, the ROI 132 defined in step 172 is modified for the consecutive frame 130 based on the spatial velocity distribution of Step 180. In the following description, an arbitrary point (x,y) inside of the ROI 132 of the current frame (i) 130 is assumed. Reconstructed tissue velocity distribution $(Vx,Vy)_i$ allows the new position of the point (x,y) to be calculated in the next consecutive frame (i+1) 130:

$$(x,y)_{i+1}=(x,y)_i+dt*(Vx,Vy)_i \qquad \text{Equation 2,}$$

wherein dt is the time between consecutive frames 130. Equation 2 is applied to landmarks identified along the main axis L, and outer and internal borders 138, 139 which define the ROI 132 shape, size, and position. The result is then used to change the shape, size, and position of the ROI 132 on the next consecutive frame 130. Therefore, the ROI 132 defined on the current frame 130 in step 172 is "stuck" with the tissue image and follows the tissue translations and deformations on the consecutive frame 130.

In Step 184, the processor 116 determines whether more image frames 130 are to be processed. If more image frames are to be processed, the flow returns to Step 174 to identify the first locations of the set of features 142 on the new current frame 130. Alternatively, the flow may return to Step 176 if the second locations of the set of features 144 are to be located on the next consecutive frame 130. If no more image frames 130 are to be processed, the flow passes to Step 186, where the processed frames of data, with the "stuck" ROI 132, are reconstructed to produce the 2-dimensional tissue dynamics in time. The reconstructed data may be displayed in a cine-loop on the display system 118 and archived to a storage medium, such as a hard disk drive internal to the ultrasound system 100 or an external disk drive. Alternatively, the method of FIG. 7 may be repeated over multiple consecutive heart cycles, and the resultant reconstructed spatial velocity distributions temporally smoothed to improve the signal-to-noise ratio.

Alternatively, the tracking process of FIG. 7 may start from an intermediate start frame within a series of stored consecutive image frames 130. In this case, the workflow of FIG. 7 is divided into two sequences. One sequence processes frames 130 from the start frame to the end frame of the series as was previously discussed. The second sequence processes frames 130 in the opposite direction, such as from the start frame to the first frame of the series. The two processing sequences may be accomplished simultaneously. After finishing both processing sequences, the results are merged to form a dataset of frames from the first frame to the end frame.

Once the tracking process is finished, the full information of the tissue dynamics is known. Therefore, the two-dimensional velocity continuous function V(x,y,t) is known in each point (x,y) inside the ROI 132 and at each time (t) along all sequences of processed frames. The results of the method of FIG. 7 allow comprehensive quantitative estimating of the following parameters:

| velocities | $Vx(x, y, t), Vy(x, y, t)$ | Equation 3, |
|---|---|---|
| displacements | $X(t) = X_0 + \int (Vx * dt),$ | Equation 4, |
|  | $Y(t) = Y_0 + \int (Vy * dt)$ |  |
| strain rates | $SR = \text{grad}(V)$ | Equation 5, |
| strains | $S(t) = S_0 + \int (SR * dt)$ | Equation 6. |

In addition to regional myocardial assessment, as illustrated in FIGS. 2–4, the method of FIG. 7 is also applicable for assessing global left ventricle (LV) functions, allowing the temporal variations of LV volume to be easily estimated. An ROI 132 is defined along the endocardium, encompassing the ventricle blood volume. The shape and position of the ROI 132 is modified, as in Step 182 ("stuck" ROI 132). As the internal border 139 of the ROI 132 was defined as the edge of endocardium on the start frame 130, the internal border 139 follows the shape changes and translations of the edge of the endocardium along the sequence of all the image frames 130. Therefore, the volume estimation of the LV may be accurately calculated over the entire heart cycle. The calculation can be based on one of the known formulas for LV volume estimation from 2D traced area, such as Simpson method and Area-Length method, for example. Temporal variations of LV volume contain important clinical information, which characterize the global LV function. By way of example only, ejection fraction (EF) is a widely used global LV parameter. The EF can be calculated as a relative change of the left ventricle volume:

$$EF(t)=(V\text{diast}-V(t))/V\text{diast} \qquad \text{Equation 7.}$$

The systolic value of the function EF(syst) is also a well known global LV parameter.

Fractional shortening, or muscle length variations during the heart cycle, is a known global indicator and may also be estimated. An ROI 132 is defined along a part of the myocardium. The "stuck" ROI 132 follows the myocardium motion of translation, rotation and deformation. Temporal variations of the ROI length L(t) represent the muscle global length variations. The L(t) contains important clinical information about the global functioning of the heart tissue. The fractional shortening (FS) is calculated as the relative muscle shortening:

$$FS(t)=(L\text{diast}-L(t))/L\text{diast} \qquad \text{Equation 8.}$$

In addition, it should be understood that the tracking process of FIG. 7 may be applied to applications other than echo-cardiography. For example, the tracking process may be used to assess tissue motion and deformation when using tagged MRI. In tagged MRI, instead of identifying the locations of features 136, such as in Step 174, MRI tags, which are artificially generated and temporally stable patterns, may be used as features.

Visual presentation of the processed data is important, allowing both quantitative assessment of the myocardium and verification of correct processing of the frames 130. Calculated parameters, including but not limited to velocities, strain rates, strains, volume variations, ejection fraction and fractional shortening may be presented in quantitative and qualitative form.

Figure 8:
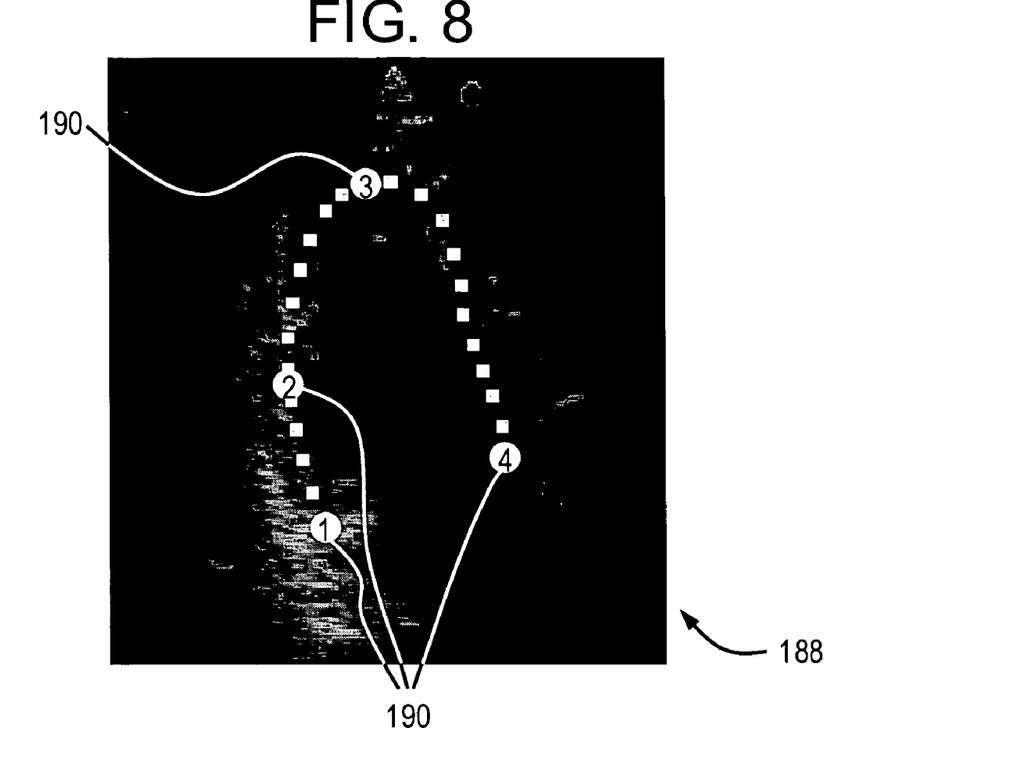
FIG. 8 illustrates an image frame of a myocardium with selected sample points labeled 1–4 formed in accordance with an embodiment of the present invention.
Figure 9:
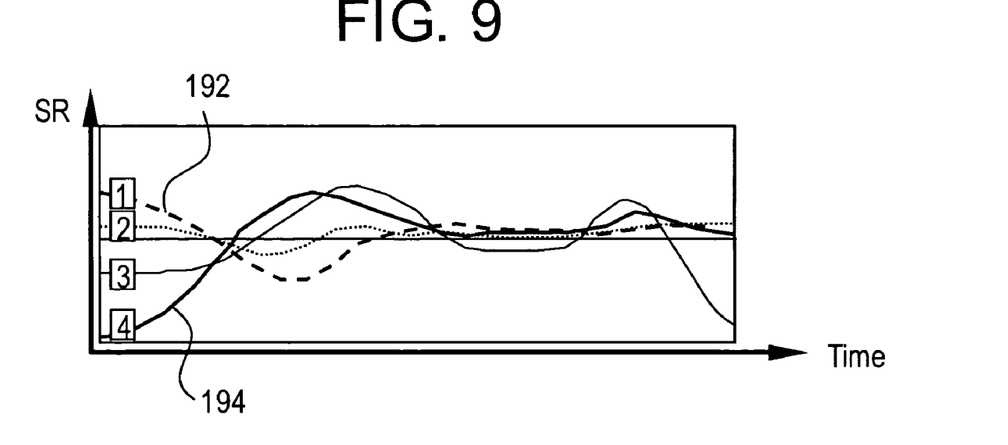
FIG. 9 illustrates a graph of longitudinal strain rate.
Figure 10:
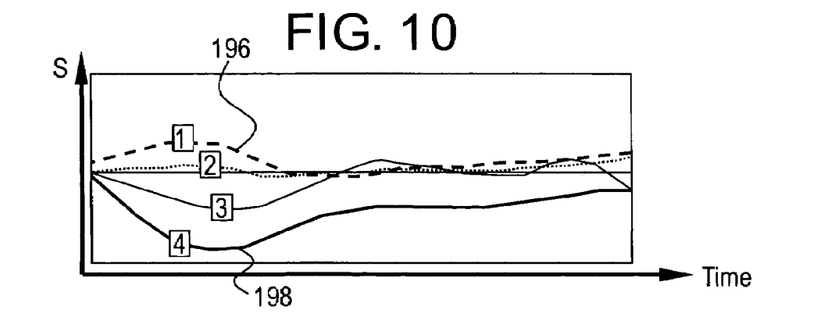
FIG. 10 illustrates a graph of longitudinal strain.
Figure 11:
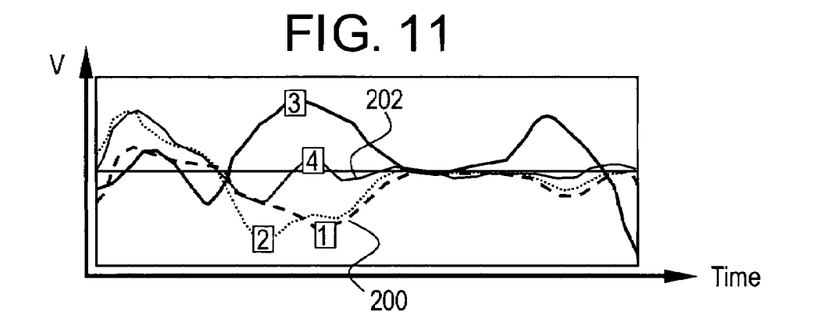
FIG. 11 illustrates a graph of longitudinal velocity.
Figure 12:
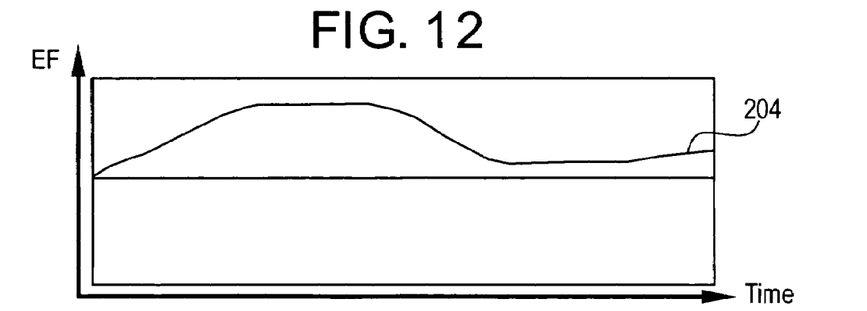
FIG. 12 illustrates a graph of ejection fraction.
Figure 13:
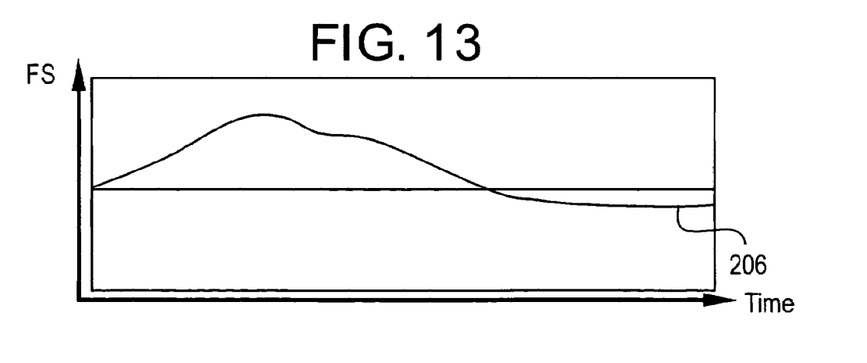
FIG. 13 illustrates a graph of fractional shortening.

FIG. 8 illustrates an image frame 188 of a myocardium with selected sample points 190 labeled 1–4. The sample points 190 may be selected by a user through the user input 124. FIGS. 9–13 illustrate quantitative graphical results of a single heart cycle. FIG. 9 illustrates longitudinal strain rate, FIG. 10 illustrates longitudinal strain, FIG. 11 illustrates longitudinal velocity, FIG. 12 illustrates ejection fraction (EF), and FIG. 13 illustrates fractional shortening (FS). The transverse components of strain, strain rate, velocity and other two-dimensional parameters may be shown as well.

Each curve illustrated on FIGS. 9–11 corresponds to one of the selected sample points 190. For example, curves 192, 196, and 200 of FIGS. 9–11, respectively, correspond to sample point 190 (1), and curves 194, 198, and 202 of FIGS. 9–11, respectively, correspond to sample point 190 (4). Curve 204 on FIG. 12 illustrates EF over the heart cycle (Equation 7), and curve 206 on FIG. 13 illustrates FS over the heart cycle (Equation 8). When displaying the data of FIGS. 8–13 on a display system 118 using color, the selected sample points 190 and the corresponding curves 192–206 may each be displayed in a different color. When using a black and white monitor or printer, the sample points 190 and curves 192–206 may be displayed with various different markers and line patterns. Alternatively, each calculated parameter could be presented in numerical tables. Spatial variations may also be graphically presented. The information allows the cardiologist to make a full quantitative assessment of the myocardium.

For qualitative presentation of results, the area within the ROI 132 on the B-mode image may be colorized in accordance with any estimated parameter. By way of example only, the estimated parameters may be a longitudinal and transverse projections (along and across the ROI 132) of the velocity components $V_L$ and $V_T$, projection of the strain rate components $SR_L$ and $SR_T$, projection of the strain components $S_L$ and $S_T$, and the like. The value of the parameter at the local point $(x,y)_i$ in the frame (i) 130 determines the color of the B-mode image at the point (x,y). Coloration according to arbitrary combinations of these parameters is possible as well. The coloration may be implemented using color pallets similar to standard ultrasound modes, such as color flow velocity imaging or tissue velocity imaging. As with other color modes, the color bar code of the selected pallet is displayed to one side of the image, allowing the estimation of the parameters' values in colorized regions.

The quality of the calculated tissue motion may also be verified, enabling the cardiologist to determine whether the tracking process (such as the process of FIG. 7) has produced valid data. Returning to FIG. 2, a set of equidistant points 134 inside the ROI 132 may be defined on the start frame 130. By way of example only, the points 134 may be shown as bullets marking the main axis L of the ROI 132. The position of each point 134 in each consecutive frame 130 is calculated using Equation 4. The points 134 are displayed with the display system 118 on each B-mode frame 130 as overlaid color bullets. The color bullets move upon animation, such as with the cine-loop, due to the temporal changes of their positions. The motion of the calculated points is observed, and a determination may be made by the echo-cardiographer as to whether the calculated points correlate with the motion of tissue patterns in their vicinity. When the tracking is successful, the colorized bullets move together with the tissue, while unsuccessful tracking shows asynchrony between the motions of the colorized bullets and the tissue. Therefore, by observing the tissue movements with the embedded color bullets, a qualitative visual estimation of the tissue tracking accuracy is achieved.

Thus, a method has been developed for quantitative myocardial assessment, allowing grading of the regional state of the myocardium. Visual observations are replaced with image processing in order to extract the information from a sequence of ultrasound B-mode images. The set of effective processing algorithms and visual presentations allow confirmation of successful tissue movement reconstruction. The method can be applied to the live scan mode as well as to a stored sequence of frames, such as cine-loop. The method is free from Doppler limitations and allows the reconstruction of full tissue dynamics, including tissue velocities and tissue contractility (strain and strain rate), and provides a quantitative, reliable, simple to use and fast tool for echo-cardiography.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for assessing tissue motion and deformation, comprising:
   accessing sequential frames of data representative of tissue;
   defining a region of interest on a current frame of data;
   identifying first locations of a set of features within said region of interest on said current frame, each feature in said set of features identifying a location within said tissue;
   locating second locations of said set of features on a consecutive frame of data; calculating velocity vectors based on said first and second locations of said set of features;
   reconstructing a continuous spatial and temporal velocity distribution by fitting said velocity vectors; and
   modifying said region of interest on said consecutive frame based on said velocity distribution to follow motion and deformation of said tissue.

2. The method of claim 1, said region of interest further comprising an outer border and an internal border, said modifying step further comprising moving said outer and internal borders on said consecutive frame to change at least one of a size, location, and shape of said region of interest.

3. The method of claim 1, said locating step further comprising using stable tissue patterns to locate said second locations.

4. The method of claim 1, said current frame being an intermediate frame within said sequential frames, said locating step further comprising simultaneously locating said second locations of said set of features on first and second consecutive frames, said first consecutive frame being acquired prior to said current frame, said second consecutive frame being acquired after said current frame.

5. The method of claim 1, further comprising:
   defining locations of equidistant points within said region of interest on said current frame, said equidistant points marking a long axis of said region of interest; and
   calculating second locations of points corresponding to said equidistant points on said consecutive frame based on said velocity distribution.

6. The method of claim 1, further comprising processing said sequential frames with said identifying, locating, calculating, reconstructing, and modifying steps in real-time as said sequential frames are acquired.

7. The method of claim 1, said locating step further comprising using similarity criteria to locate said second locations, said similarity criteria being one of Sum of Absolute Differences and cross-correlation technique.

8. The method of claim 1, further comprising:
   said locating step further comprising using stable tissue patterns of said each feature to locate said second locations;
   grading a similarity of said stable tissue patterns to determine a confidential weight for said each feature; and said reconstructing step further comprising fitting said velocity vectors with a continuous function using said confidential weights to reconstruct said velocity distribution.

9. The method of claim 1, further comprising:
said region of interest being identified along a portion of a myocardium according to its anatomical structure;
identifying an end diastolic length of said region of interest during at least one heart cycle;
identifying a current length of said region of interest on said current frame; and
calculating a fractional shortening of said tissue based on said end diastolic and current lengths.

10. The method of claim 1, further comprising:
calculating at least one parameter based on said velocity distribution, said at least one parameter being one of a regional velocity, regional displacement, regional strain rate, regional strains and regional temporal sequences;
displaying said frames in B-mode on a display; and
coloring ultrasound data within said region of interest based on said at least one parameter.

11. The method of claim 1, said sequential frames being stored on a storage medium prior to said accessing step.

12. The method of claim 1, further comprising:
selecting at least one point within said region of interest;
calculating at least one parameter based on said velocity distribution corresponding to said at least one point, said at least one parameter being one of a longitudinal strain rate, longitudinal strain, and longitudinal velocity, said at least one parameter being calculated over at least one heart cycle; and
displaying a temporal variation of said at least one parameter on a graph on a display system, each said at least one point being represented by a line on said graph.

13. The method of claim 1, said sequential frames including MRI data, said method further comprising MRI tags representing temporally stable patterns within said tissue.

14. The method of claim 1, said sequential frames comprising three-dimensional ultrasound data.

15. A method for assessing left ventricle function, the method comprising:
accessing stored frames of data representative of at least one heart cycle;
identifying a region of interest on a current frame of data, said region of interest including an outline along an endocardium of a left ventricle;
identifying first locations of features within said region of interest on said current frame, each said feature representing said endocardium;
estimating second locations of said features on at least one adjacent frame of data;
calculating velocity vectors based on said first and second locations of said features: and
modifying said region of interest on said at least one adjacent frame of data based on said velocity vectors calculated from said first and second locations to follow motion and deformation in said left ventricle.

16. The method of claim 15, further comprising calculating a volume of said left ventricle for each said stored frames of data after said region of interest has been modified.

17. The method of claim 15, further comprising:
calculating a volume of said left ventricle for each frame of data after said region of interest has been modified;
identifying a maximum volume;
identifying a minimum volume; and
calculating an ejection fraction based upon said maximum and minimum volumes.

18. An ultrasonic system for assessing tissue motion and deformation, comprising:
a transmitter driving transducers within a probe to emit pulsed ultrasonic signals into a body;
a receiver receiving echoes detected by said transducers, said echoes being backscattered from tissue within the body;
a memory storing said echoes as sequential frames of data; and
a processor accessing said sequential frames from said memory and defining a region of interest on a current frame, said processor identifying first locations of a set of features on said current frame within said region of interest and locating second locations of said set of features on a consecutive frame, said processor calculating velocity vectors based on said first and second locations and reconstructing a continuous spatial and temporal velocity distribution by fitting said velocity vectors, said processor modifying said region of interest on said consecutive frame based on said velocity distribution to follow motion and deformation of said tissue.

19. The system of claim 18, further comprising:
said processor further defining locations of equidistant points within said region of interest on said current frame, said processor calculating second locations of points corresponding to said equidistant points on said consecutive frame based on said velocity distribution; and
a display system displaying said current and consecutive frames of data with said equidistant points and said points, respectively, in a cine-loop to determine successful tracking of said tissue.

20. The system of claim 18, further comprising:
said processor further defining said region of interest as a myocardial outline and selecting at least one point within said region of interest, said processor calculating at least one parameter based on said velocity vectors corresponding to said at least one point, said at least one parameter being one of a longitudinal strain rate, longitudinal strain, and longitudinal velocity, said at least one parameter being calculated over at least one heart cycle; and
a display system displaying said at least one parameter in a numerical graphical display.

21. The system of claim 18, further comprising a user input for inputting region of interest data, said region of interest data being used by said processor to define said region of interest on said current frame.

* * * * *